United States Patent
Nahrwold

(10) Patent No.: US 11,739,036 B2
(45) Date of Patent: Aug. 29, 2023

(54) PROCESS TO OBTAIN 3-PHENYLPROPAN-L-OL FROM NATURAL SOURCES

(71) Applicant: Minasolve Solutions sprl, Mont-Saint-Guibert (BE)

(72) Inventor: Markus Nahrwold, Minden (DE)

(73) Assignee: Minasolve Solutions sprl, Mont-Saint-Guibert (BE)

( * ) Notice: Subject to any disclaimer, the term of this patent is extended or adjusted under 35 U.S.C. 154(b) by 0 days.

(21) Appl. No.: 17/294,862

(22) PCT Filed: Nov. 22, 2019

(86) PCT No.: PCT/EP2019/082300
§ 371 (c)(1),
(2) Date: May 18, 2021

(87) PCT Pub. No.: WO2020/104682
PCT Pub. Date: May 28, 2020

(65) Prior Publication Data
US 2022/0009863 A1    Jan. 13, 2022

(30) Foreign Application Priority Data
Nov. 22, 2018  (BE) .................. 2018/5816

(51) Int. Cl.
*C07C 29/17*   (2006.01)
*C07C 29/86*   (2006.01)
*C07C 29/80*   (2006.01)

(52) U.S. Cl.
CPC ............ *C07C 29/175* (2013.01); *C07C 29/80* (2013.01); *C07C 29/86* (2013.01)

(58) Field of Classification Search
CPC .................................................. C07C 29/175
See application file for complete search history.

(56) References Cited

FOREIGN PATENT DOCUMENTS

| | | |
|---|---|---|
| DE | 102 33 339 A1 | 11/2003 |
| WO | 2020104682 A1 | 5/2020 |

OTHER PUBLICATIONS

Walter, K. et al. machine translation of Patent No. DE10233339A1, Nov. 6, 2003, pp. 1-7 (Year: 2003).*
Wong, Y. C. et al. "Extraction of Essential Oil from Cinnamon (*Cinnamomum zeylanicum*)" Orient. J. Chem., vol. 30(1), 37-47 (2014) (Year: 2014).*
Lee, H-S. "Anticoagulant Properties of the Active Compound Derived from Cinnamomum cassia Bark" Food Sci. Biotechnol. vol. 16 , No. 2, pp. 218-222 (2007) (Year: 2007).*
Kim, H-O. et al. "Inactivation of *Escherichia coli* O157:H7 by cinnamic aldehyde purified from Cinnamomum cassia shoot" Food Microbiology 21 (2004) 105-110 (Year: 2004).*
ISR/WO dated Feb. 7, 2020 for parent application No. PCT/EP2019/082300.
Al-Bayati et al., "Isolation, identification, and purification of cinnamaldehyde from Cinnamomum zeylanicum bark oil. An antibacterial study", Pharmaceutical Biology,vol. 47, No. 1, Jan. 1, 2009 (Jan. 1, 2009), p. 61-66.
EU. Restricted Substances: Annex III, Regulation 1223/2009/EC on Cosmetic Products, as amended by Regulation (EU) 2020/1683, Nov. 13, 2020; updated as of May 6, 2021.

* cited by examiner

*Primary Examiner* — Medhanit W Bahta
(74) *Attorney, Agent, or Firm* — Vorys, Sater, Seymour and Pease LLP

(57) ABSTRACT

The present invention relates to a process for the manufacturing of 3-phenylpropan-1-ol, from nature derived starting material, wherein said nature derived starting material comprises not less than 80 wt. % of cinnamaldehyde. In another aspect, the present invention relates to the process, which further comprises the steps: a) conversion of cinnamaldehyde as starting material to 3-phenylpropan-1-ol by a catalytic hydrogenation; b) optional purification of the 3-phenylpropan-1-ol by alkaline water extraction; c) distillation of 3-phenylpropan-1-ol. In a third aspect the present invention relates to use of 3-phenylpropan-1-ol obtained by the process of the invention in perfumes and/or personal care and/or cleaning products.

5 Claims, No Drawings

PROCESS TO OBTAIN 3-PHENYLPROPAN-1-OL FROM NATURAL SOURCES

FIELD OF THE INVENTION

The present invention relates to an improved process to obtain pharmaceutical, cosmetic or food ingredient from a natural source. More particularly, this invention relates to the production of 3-phenylpropan-1-ol from cinnamaldehyde obtained from nature-derived starting material, such as essential oil and/or plant extract.

BACKGROUND

Petrochemicals are a large group of chemicals derived from petroleum and natural gas. Petrochemicals are widely used in the food, chemical and pharmaceutical industry and agriculture. Although the petrochemicals give us innumerable useful products, they can also be harmful to the health of living beings and the earth's ecosystem. Most of these chemicals when released can exhibit detrimental effects on the environment, manifested as air, water and soil pollution. Once present in ecosystem, the petrochemical pollutants enter the food chain and pose a serious health risk for humans, animals and plants. Petrochemical industry is an important source for the principal greenhouse gases responsible for global warming. Other environmental impacts include ozone layer depletion, acid rain, air pollution, etc.

For these reasons, there is an increasing trend in many industries to replace petrochemical ingredients by nature-derived products. Especially antimicrobial agents and preservatives have come under debate for their possibly long persistence in the environment, and for their potentially disturbing effects on human health. Many eco-certified personal care products are therefore preserved with the help of natural or nature-identical organic acids, such as benzoic acid, salicylic acid and sorbic acid. However, these acids are only effective in an acidic environment, typically at pH-levels below 6, which significantly limits their application. The choice of natural or nature-derived antimicrobial agents being effective at higher pH-levels is limited.

Aromatic alcohols appear to be suitable candidates, since their antimicrobial effects are not significantly altered by a high pH value. The most commonly used representative is phenoxyethanol, which is a petrochemical preservative. Alternatives are benzyl alcohol, which is a potentially nature-derived component that is listed as skin allergen in Annex III of the European Cosmetic Regulation, as well as phenethyl alcohol—a nature-derived aroma component with noticeable odor.

3-Phenylpropan-1-ol (INCI name: Phenylpropanol) is an aromatic alcohol with a mild and pleasant odor. 3-Phenylpropan-1-ol is used as fragrance ingredient in perfumes and personal care products. Recently, the interest for this compound increased for its antimicrobial properties. Furthermore, the allergen potential of Phenylpropanol is relatively low (SCCS—Scientific Committee on Consumer Safety—Opinion on fragrance allergens in cosmetic products, 26-27 Jun. 2012), which makes it particularly attractive as ingredient for personal care applications. Although being part of the natural flavor of ripe strawberries and the natural fragrance of e.g. hyacinths, 3-phenylpropan-1-ol cannot be economically extracted from these natural sources due to its low content inside the plant materials. Therefore, 3-phenylpropan-1-ol is commonly manufactured by catalytic hydrogenation of cinnamaldehyde on a precious metal or transition metal catalyst. As an example, the German patent application DE10233339 describes the hydrogenation of cinnamaldehyde under an atmosphere of 1-100 bar of hydrogen gas, catalysed by Molybdenum-promoted sponge Nickel catalysts ("Raney-Nickel"). The starting material "cinnamaldehyde" is conventionally obtained by an aldol condensation of the two petrochemical substances benzaldehyde and acetaldehyde. However, aldol condensation ensures the yields typically up to 70-80%, and reactions are often not selective towards a particular isomer. Moreover, benzaldehyde is a significant pollutant, while acetaldehyde is listed as a Group 1 carcinogen, by International Agency for Research on Cancer (IARC). Therefore, the prior art lacks a safer, industrially applicable method to produce phenylpropanol.

Cinnamaldehyde occurs abundantly in some plant species. It can be isolated in an enriched form, e.g. from the barks and twigs of *Cassia* trees (*Cinnamomum cassia*) and Cinnamon trees (*Cinnamomum verum*). The cinnamaldehyde can be obtained e.g. via steam distillation or by extraction with suitable extraction solvents, like supercritical carbon dioxide or other volatile organic solvents. The corresponding essential oils ("*Cassia* oil", "Cinnamon oil") or extracts contain up to 90 wt. % of Cinnamaldehyde, together with a large variety of further volatile components, mainly terpenes and phenols.

However, obtaining pure cinnamaldehyde from such complex mixtures requires extensive purification, typically involving many steps, which makes such process inapplicable in the industry. Furthermore, the natural cinnamaldehyde cannot be easily purified by distillation, since it forms various azeotropes with other natural components, which can be difficult to purify. Finally, most of the components naturally occurring in *Cassia* and Cinnamon essential oils and related extracts are known fragrance allergens and listed as such in Annex III of the European Cosmetic Regulation. It is therefore important to ensure their absence in products derived from these natural materials, especially if they are intended to be used for applications on human skin.

The present invention aims to resolve at least some of the problems and disadvantages related to production of 3-phenylpropan-1-ol. The aim of the invention is to provide an industrially feasible method which is less hazardous for living organisms and which is less detrimental to the environment. At the same time, the present invention aims for utilization of the naturally occurring cinnamaldehyde from a plant source.

SUMMARY OF THE INVENTION

The present invention relates to a process of preparation of 3-phenylpropan-1-ol from cinnamaldehyde obtainable from a natural source, such as essential oils and concentrates rich in cinnamaldehyde.

In a first aspect, the present invention relates to a process for manufacturing of 3-phenylpropan-1-ol from nature derived starting material, wherein said nature derived starting material comprises not less than 80 wt. % of cinnamaldehyde.

The term "nature derived", as used herein, means obtainable from nature, particularly by processing of plant material and plant isolates, such as essential oils, extracts and purified fractions thereof.

The term "cinnamaldehyde", as used herein, refers to phenyl-propane aldehyde with IUPAC name 3-phenylprop-2-enal and molecular formula ($C_9H_8O$). The CAS registry number of cinnamaldehyde is 104-55-2.

The term "starting material", as used herein, means a raw material, intermediate, or a reactant that is used in the production of a substance of interest, and that is incorporated as a significant structural fragment and/or in a significant amount into the structure of the substance of interest.

The present invention offers the efficient method for utilization of cinnamaldehyde directly from a plant isolate containing the cinnamaldehyde in a concentration higher than 80 wt. %. This was not possible by the prior art, as the prior art methods required cinnamaldehyde in its pure form, which made the utilization of nature derived compound non-feasible.

In a preferred embodiment, said nature derived starting material comprises not less than 90 wt. % of cinnamaldehyde, preferably not less than 95 wt. % of cinnamaldehyde. In a further preferred embodiment, said nature derived starting material is essential oil or essential oil concentrate obtained from Cinnamon bark and/or *Cassia* bark.

The term "essential oil", as used herein, means a concentrated hydrophobic liquid containing volatile (defined as "the tendency of a substance to vaporize") aroma compounds from plants, particularly aromatic plants. Essential oils are typically multicomponent mixtures of plant secondary metabolites, belonging to the classes of terpenes (mono- and sesquiterpenes), phenylpropanes and coumarins.

In a further preferred embodiment, said nature derived starting material is essential oil concentrate obtained from Cinnamon bark and/or *Cassia* bark.

The term "concentrate", as used herein, means extract, isolate or concentrated essential oil, obtainable by a suitable extraction and or purification technique, such as, but not limited to solvent extraction, distillation, fractional distillation, steam distillation, extraction with liquid and/or supercritical gases, purification by chromatography (partition, adsorbent and size exclusion chromatography), concentration on suitable adsorbent material, expression, cold pressing, and the like.

In a further preferred embodiment, the process of the invention further comprises the steps: a) conversion of cinnamaldehyde in starting material to 3-phenylpropan-1-ol by a catalytic hydrogenation; b) optional purification of the 3-phenylpropan-1-ol by alkaline water extraction; c) distillation of 3-phenylpropan-1-ol.

In a further preferred embodiment, the step a) the catalytic hydrogenation is carried out in the presence of a nickel catalyst.

In a further preferred embodiment, the step a) the catalytic hydrogenation is carried out under a hydrogen pressure of between 1 bar and 100 bar.

In a further preferred embodiment, the step a) yields max. 0.5% cinnamaldehyde and/or max. 0.5% cinnamyl alcohol and/or max. 0.5% 3-phenylpropionaldehyde and/or max. 0.5% 3-cyclohexylpropan-1-ol, as by-products and/or impurities, which complicate the purification of 3-phenylpropan-1-ol.

In a further preferred embodiment, the step b) is carried out by washing with alkaline water solution with optional addition of an organic solvent.

In a further preferred embodiment, said alkaline water solution is obtained by adding of a base selected from at least one alkali or earth alkali hydroxide to water. In a further preferred embodiment, said organic solvent selected from heptane, toluene, tert-butyl methyl ether, 4-methyl tetrahydrofuran. In a further preferred embodiment, the step c) allows obtaining 3-phenylpropan-1-ol of a purity of not less than 95 wt. %. In a further preferred embodiment, the obtained 3-phenylpropan-1-ol is free of fragrance allergens listed in Annex III of the European Cosmetic Regulation. In a further preferred embodiment, the obtained 3-phenylpropan-1-ol has an odor comparable to 3 phenylpropan-1-ol produced from petrochemical raw materials.

In another embodiment, 3-phenylpropan-1-ol, obtained by the process of the invention can be used in perfumes and/or personal care and/or cleaning products. In another embodiment, 3-phenylpropan-1-ol, obtained by the process of a) conversion of cinnamaldehyde in starting material to 3-phenylpropan-1-ol by a catalytic hydrogenation; b) optional purification of the 3-phenylpropan-1-ol by alkaline water extraction; c) distillation of 3-phenylpropan-1-ol is used in perfumes and/or personal care and/or cleaning products, whereas said perfumes and/or personal care and/or cleaning products are self-preserved due to the presence of nature-derived 3-phenylpropan-1-ol.

DETAILED DESCRIPTION OF THE INVENTION

The present invention concerns the process for preparation of 3-phenylpropan-1-ol from cinnamaldehyde obtainable from a natural source.

In particular, the present invention provides an efficient and industrially applicable method for obtaining 3-phenylpropan-1-ol as fragrance and anti-microbial ingredient useful in household, cosmetics, food and pharmaceutical industry. The process is directed to utilization of cinnamaldehyde from natural sources, such as essential oils, essential oil concentrates, extracts and other plant isolates.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a starting material" refers to one or more than one starting material.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may refer to it. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the present invention relates to a process for manufacturing of 3-phenylpropan-1-ol from nature derived starting material, wherein said nature derived starting material comprises not less than 80 wt. % of cinnamaldehyde.

Cinnamaldehyde is a secondary plant metabolite, present in various plant species where it predominantly occurs as the trans (E) isomer. It gives cinnamon its flavor and odor. Cinnamaldehyde is a Standardized Chemical Allergen. The physiologic effect of cinnamaldehyde is by means of increased histamine release, and cell-mediated immunity, thus its chemical classification is "Allergens". Concentrated cinnamaldehyde is a skin irritant, and the chemical is toxic in large doses, but no agencies suspect the compound is a carcinogen or poses a long-term health hazard. Most cinnamaldehyde is excreted in urine as cinnamic acid, an oxidized form of cinnamaldehyde.

Cinnamaldehyde occurs abundantly in some plant species, for example in the bark of cinnamon trees and other species of the genus *Cinnamomum* like camphor and *cassia*. These trees are the natural source of cinnamon, and the essential oil of cinnamon bark is about 90% cinnamaldehyde. Thus, cinnamaldehyde can be isolated in an enriched form, e.g. from the barks and twigs of *Cassia* trees (*Cinnamomum cassia*) and Cinnamon trees (*Cinnamomum verum*). The cinnamaldehyde can be obtained e.g. via steam distillation or by extraction with suitable extraction solvents, like supercritical carbon dioxide or other volatile organic solvents. The corresponding essential oils ("*Cassia* oil", "Cinnamon oil") or extracts contain up to 90 weight-% of Cinnamaldehyde, together with a large variety of further volatile components, mainly terpenes and phenols. Table 1 gives an overview of the typical natural constituents of *Cassia* and Cinnamon bark essential oils.

TABLE 1

Components of two samples of Cassia essential oil and one sample of Cinnamon essential oil (area-% by GC-FID)

| Component | Cassia bark oil (China) | Cassia oil (Indonesia) | Cinnamon bark oil (Sri Lanka) |
|---|---|---|---|
| Benzaldehyde | 1.4% | 0.7% | 0.8% |
| Cadinene, delta- | 0.3% | 7.6% | |
| Camphene | | 3.1% | 0.7% |
| Caryophyllene | 0.3% | 3.2% | 3.6% |
| Cinnamaldehyde, trans- | 67.6% | 45.8% | 68.2% |
| Cinnamaldehyde, cis- | 0.7% | 0.6% | 0.5% |
| Cinnamyl acetate | 4.9% | 3.2% | 5.4% |
| Copaene, alpha- | 0.7% | 0.6% | |
| Coumarin | 3.6% | | 3.5% |
| Cymene, para- | | | 1.2% |
| Eucalyptol | | 5.7% | 2.7% |
| Eugenol | | | 3.7% |
| Limonene | | 4.0% | 1.8% |
| Linalool, beta- | | 0.4% | 3.0% |
| Methoxycinnamaldehyde, ortho- | 15.4% | 4.4% | |
| Phellandrene, alpha- | | | 0.1% |
| Pinene, alpha- | 0.2% | 3.8% | 2.1% |
| Pinene, beta- | 0.1% | 0.8% | 0.7% |
| Phenylethylalcohol | 0.8% | 1.7% | 1.0% |
| Salicylaldehyde | 0.4% | | |
| Terpinene, alpha- | 0.6% | 4.4% | |
| Terpineol, 4- | | 1.6% | |
| Terpinolene, alpha- | | 0.6% | |

The process of the invention offers a method of utilization of cinnamaldehyde from such complex mixtures by avoiding extensive purification steps, known in the prior art.

The natural cinnamaldehyde cannot be easily purified by distillation, since it forms various azeotropes with other natural components. Several azeotropes of cinnamaldehyde with other components of essential oils are described in the literature, e.g. those with cinnamyl alcohol, 3-phenylpropanol, methyl cinnamate, safrole, anethole, isoeugenol, carvacrol, thymol, butyl benzoate, isobutyl benzoate, phenyl ether and isoamyl benzoate (as a reference: "Advances in Chemistry Series No 60, Azeotropic Data", American Chemical Society, 1952, page 232). A person skilled in the art would therefore expect that cinnamaldehyde can be obtained from extracts or essential oils only in the form of an azeotropic mixture together with additional components. Even if some of these azeotropes may be broken by common techniques, such as adjustment of the pressure or addition of further components, the overall technical procedure remains effortful.

The process of invention solves the above-mentioned problem, as there is no pre-purification step of a nature derived starting material required. Namely, the process of invention offers an efficient and industrially applicable utilization of cinnamaldehyde from nature derived essential oils, concentrates and isolates. It has been surprisingly found that nature derived starting material can be subjected to a simple processing, preferably concentration of cinnamaldehyde. Said processing is distillation, chromatographical separation, extraction and the like, in order to obtain the nature derived starting material which contains more than 80 wt. % cinnamaldehyde, preferably more than 90 wt. % cinnamaldehyde, and most preferably more than 95 wt. % cinnamaldehyde. If the original natural extracts or essential oils contains already more than 80% cinnamaldehyde, the distillation can be omitted, and the material can be directly used in the next technical step.

In the preferred embodiment, the starting material containing cinnamaldehyde is obtained by a distillation of the essential oil or the natural extract containing cinnamaldehyde. Said distillation process can be carried out at any pressure, preferably in vacuo at 500 mbar-0.001 mbar, most preferred at 30-0.1 mbar. In further preferred embodiment, the efficient separation can be enhanced e.g. by using an appropriate column. It should be understood that a skilled person can conduct said distillation in batch-wise, continuous or semi-continuous mode, or any suitable optimization known in the prior art, without departing from the scope of the invention.

In a further preferred embodiment, cinnamaldehyde is obtained from a distillation of essential oil from *Cassia* and/or *Cinnamon* species. In a particularly preferred embodiment, said starting material is concentrate obtained by distillation of the essential oil from *Cassia* and/or *Cinnamon* species.

In further preferred embodiment, said nature derived cinnamaldehyde can be converted to 3-phenylpropan-1-ol by means of the following sequence of simple technical steps: a) conversion of cinnamaldehyde as starting material to 3-phenylpropan-1-ol by a catalytic hydrogenation; b) optional purification of the 3-phenylpropan-1-ol by alkaline water extraction; c) distillation of 3-phenylpropan-1-ol.

In a further preferred embodiment, the step a) the catalytic hydrogenation is carried out in the presence of a nickel catalyst.

According to the process of the invention, the conversion of cinnamaldehyde present in nature derived starting material to 3-phenylpropan-1-ol is achieved by hydrogenation. Said hydrogenation can be carried out either in the presence of hydrogen gas or by using another component that releases hydrogen. The reaction is typically carried out under pressures of between 1 bar and 100 bar hydrogen, preferably between 10 bar and 50 bar. The temperature of the reaction is typically chosen between 0° C. and 200° C., preferably between 30° C. and 150° C., most preferred between 50° C. and 100° C. In a further preferred embodiment the step a) the catalytic hydrogenation is carried out under a hydrogen pressure of between 1 bar and 100 bar.

In a further preferred embodiment, the step a) yields max. 0.5% cinnamaldehyde and/or max. 0.5% cinnamyl alcohol and/or max. 0.5% 3-phenylpropionaldehyde and/or max. 0.5% 3-cyclohexylpropan-1-ol, as by-products and/or impurities, which complicate the purification of 3-phenylpropan-1-ol.

In a further preferred embodiment, the step b) is carried out by washing with alkaline water solution with optional addition of an organic solvent.

In a further preferred embodiment, said alkaline water solution is obtained by adding of a base selected from at least one alkali or earth alkali hydroxide to water.

In a further preferred embodiment, said organic solvent selected from heptane, toluene, tert-butyl methyl ether, 4-methyl tetrahydrofuran.

In a further preferred embodiment, the step c) allows obtaining 3-phenylpropan-1-ol of a purity of not less than 95 wt. %.

The hydrogenation reaction of cinnamaldehyde to Phenylpropanol can be mediated by any metal catalyst suitable for transforming C=C-double bonds into C—C single bonds and CH=O carbonyl functions into CH2-OH alcohol functions. The reaction can be performed either in one step or in a sequence of several hydrogenation steps. Preferably the reaction is carried out in one single hydrogenation step. In the preferred embodiment, the hydrogenation reaction is stopped, as soon as cinnamaldehyde from the starting material and intermediates cinnamyl alcohol and 4-phenypropional are present at concentrations of less than 1%, most preferably less than 0.5%. A low content of cinnamaldehyde, cinnamyl alcohol and 4-phenylpropional simplifies the subsequent purification of 3-phenylpropan-1-ol, because an occurrence of azeotropes is avoided.

In a preferred embodiment of the invention, the hydrogenation conditions are adjusted in way that the formation of 3-cyclohexylpropan-1-ol is largely avoided. This potential by-product may originate from the saturation of the aromatic ring of cinnamaldehyde. It can lead to an undesired additional odor of the final product 3-phenylpropan-1-ol.

It was found that phenolic impurities such as eugenol and ester impurities such as 3-phenylpropyl-1-acetate can further complicate the final purification of 3-phenylpropan-1-ol by distillation. The yield of the pure 3-phenylpropan-1-ol decreases in the presence of these impurities, because they have either similar boiling points as 3-phenylpropan-1-ol and/or form azeotropic mixtures with the target product. Consequently, the distillation must be carried out either at higher reflux ratios or by using a more efficient separation column, both leading to higher expenses. In a further preferred embodiment, the phenolic and ester impurities are preferentially removed in an optional purification step, preferably extraction by aqueous washing, in order to avoid high losses of material during purification.

The aqueous washing of the crude 3-phenylpropan-1-ol can be carried in the presence or in the absence of an additional solvent. Since Phenylpropanol and water have a similar density of about 1 g/ml, the aqueous washing is preferably carried out in the presence of at least one organic solvent. In a further preferred embodiment, the organic solvent is not completely miscible with water. Suitable solvents comprise, but are not limited to, aromatic hydrocarbons such as toluene and xylene, ethers such as tert-butyl methyl ether and 4-methyl-tetrahydrofuran, or aliphatic hydrocarbons such as heptane and hexane. The washing steps and the phase separations are typically carried out at temperatures between 0° C. and 100° C.

In a further preferred embodiment, the aqueous washing solution should contain at least one organic and/or inorganic alkaline component suitable for the removal of carboxylic acids and/or esters and/or phenols. Preferably, the component is selected from strong alkaline salts that can saponify esters and deprotonate phenols, thus enabling the removal of these potential impurities. Most preferably the washing solution contains at least one alkali hydroxide or earth alkali hydroxide.

In another embodiment of this invention, the aqueous washing solution contains additional salts that increase the density of the aqueous solution. The larger difference in the densities of the aqueous phase and the organic phase may lead to a faster phase separation. The additional salts can be chosen from, but are not limited to, alkali and/or earth alkali halides and/or sulphates.

Depending on the composition of the nature derived starting material, the crude 3-phenylpropan-1-ol obtained after hydrogenation may occasionally not contain any significant amounts of the impurities which can be removed by an alkaline washing step. In these cases, the aqueous washing steps can be omitted.

Most of the components naturally occurring in *Cassia* oil, Cinnamon oil and related extracts are known fragrance allergens and listed as such in Annex III of the European Cosmetic Regulation. It is therefore important to ensure their absence in products derived from these natural materials, especially if they are intended to be used for applications on human skin.

Moreover, most of the volatile components derived from *Cassia* and Cinnamon bark exhibit a characteristic odor, which also remains after hydrogenation of these components. It is therefore important, especially for applications in perfumes, to exclude any volatile impurities having a strong characteristic odor. By means of that, it can be ensured that the nature-derived 3-phenylpropan-1-ol exhibits an odor comparable to the petrochemical standard. In a preferred embodiment, the obtained 3 phenylpropan-1-ol has an odor comparable to 3 phenylpropan-1-ol being produced from petrochemical raw materials. More particularly, the obtained 3 phenylpropan-1-ol is characterized by a pleasant odour that can be described as "spicy, cinnamon, fruity, floral and honey-like with balsamic nuances" (Gerard Mosciano, Perfumer&Flavorist 20, No. 6, 49, 1995.)

The final purification of nature-derived 3-phenylpropan-1-ol is preferably carried out by distillation in vacuo at between 500 mbar and 0.001 mbar, most preferred between mbar and 0.1 mbar. A more efficient separation can be achieved e.g. by using an appropriate column. The distillation can be carried out batch-wise, continuous or semi-continuous. The distilled nature-derived 3-phenylpropan-1-ol typically has a purity of at least 95 wt. %, preferably at least 98 wt. %, most preferred at least 99 wt. %.

The nature-derived 3-phenylpropan-1-ol obtained by a process according to this invention is suitable as ingredient for perfumes, personal care products and other products. Due to its high purity, the odor and the technical performances are equivalent to those of conventional 3-phenylpropan-1-ol obtained from petrochemical starting materials.

In a further embodiment of this invention, 3-phenylpropan-1-ol obtained by a process according to this invention is free of fragrance allergens listed in Annex III of the European Cosmetic Regulation.

In a preferred embodiment of the invention, the process allows obtaining 3-phenylpropan-1-ol which is free of allergens and typical odor-affecting impurities. 3-Phenylpropan-1-ol obtained in the process of the invention is suitable for use in cosmetics, household and food products, pharmaceuticals, and the like. In particular, such phenylpropan-1-ol is suitable for perfumes, personal care products and cleaning products.

In a preferred embodiment, 3-phenylpropan-1-ol of the invention is used in a concentration not more than 5 wt. % in a personal care or household products, preferably in a concentration of about 1 wt. %. In a perfume industry, 3-phenylpropan-1-ol obtained by the process of the invention can be used in any concentration which is suitable for a desired odor profile to be achieved, without departing from the scope of the present invention.

In a further preferred embodiment, such perfume, personal care or household product composition is self-preserved, due to the fact that 3-phenylpropan-1-ol obtained by the process of the invention exerts an anti-microbial activity. In a further preferred embodiment, no additional antimicrobial preservative is necessary in composition of the product which comprises 3-phenylpropan-1-ol obtained by the process of the present invention.

In a further embodiment of the invention, allergen causing impurities or substances leading to olfactory off-notes of nature-derived 3-phenylpropan-lol are removed by means of treatment with solid adsorbents, such as—but not limited to—activated carbon, mineral adsorbents or ion exchange resins.

In another embodiment of the invention, allergen causing impurities or substances leading to olfactory off-notes of nature-derived 3-phenylpropan-lol are removed by means of treatment with complexation agents capable of binding to specific molecules. Non-limiting examples comprise cyclodextrins and their derivatives.

In yet another embodiment of the invention, allergen causing impurities or substances leading to olfactory off-notes of nature-derived 3-phenylpropan-lol are removed by means of steam stripping.

The present invention will now be further exemplified with reference to the following example(s). The present invention is in no way limited to the following examples, or preferred embodiments stated in the text. On the contrary, disclosed products, methods and applications according to the present invention may be realized in many different ways without departing from the scope of invention.

EXAMPLES

Example 1

Cassia Bark Oil of Chinese origin (1057 g, containing 76% cinnamaldehyde) was fractionally distilled over a column with dimensions 3×65 cm, filled with 4 mm-Wilson spirals. The distillation was carried out in a vacuum of 7-9 mbar, and the main fractions were collected at boiling temperatures of 102-107° C. The following fractions of distilled material were obtained (% GC-FID)

| Fraction | Weight | Cinnamaldehyde | Cinnamyl acetate |
| --- | --- | --- | --- |
| 1 | 26.83 g | 42.64% | 0.33% |
| 2 | 57.76 g | 76.51% | 0.89% |
| 3 | 50.73 g | 86.26% | 1.18% |
| 4 | 109.83 g | 88.39% | 1.08% |
| 5 | 105.50 g | 92.63% | 1.18% |
| 6 | 123.97 g | 91.63% | 1.28% |
| 7 | 37.53 g | 93.88% | 1.31% |
| 8 | 115.37 g | 94.13% | 1.43% |
| 9 | 91.73 g | 95.31% | 1.67% |
| 10 | 69.80 g | 94.42% | 1.86% |
| 11 | 3.95 g | 94.33% | 2.72% |
| Residue | 235.62 g | 30.69% | 9.99% |

The obtained results confirm the difficulty to separate cinnamyl acetate and cinnamaldehyde by means of fractional distillation.

The fractions 6-10 (647 g) were combined and contained an average of 93.8% (GC-FID) cinnamaldehyde and 1.5% (GC-FID) cinnamyl acetate. These combined fractions were hydrogenated in a 1000 mL stainless steel autoclave at 75-80° C. under an atmosphere of 20 bar hydrogen gas in the presence of sponge Nickel catalyst (50 g, Johnson Matthey, Type A-7000). The hydrogenation was stopped after 48 hours, when the starting material and the intermediates were sufficiently consumed. The filtered crude product contained 3-phenylpropyl-1-acetate (1.1 area-% GC-FID). The filtrate was diluted with 4-methyl-tetrahydrofuran and washed with 10% aqueous sodium hydroxide solution and water. The organic phase was concentrated, and the obtained oily residue contained less than 0.1% of 3-phenylpropyl-1-acetate, which is the hydrogenation product of cinnamyl acetate. Fractional distillation of the residue in vacuo (7-8 mbar, 98-101° C.) afforded 3-phenylpropan-1-ol (492 g, 99.7 area-% GC-FID). The odor of the obtained distilled fractions was tested on paper stripes by an expert panel. Said expert panel constituted of 5 panelists, of which at least 4 had to agree that the aroma complies with the request, in order to have a compliant aroma. Each fraction was compared to a reference of petrochemical-derived 3-phenylpropan-1-ol. The following results were obtained:

| Fraction | Weight | 3-Phenylpropan-1-ol | 3-phenylpropyl-1-acetate | Odor compared to reference standard |
| --- | --- | --- | --- | --- |
| 1 | 24.43 g | 89.86% | 0.63% | Does not comply |
| 2 | 26.17 g | 94.51% | 0.61% | Does not comply |
| 3 | 20.3 g | 98.34% | 0.63% | Does not comply |
| 4 | 24.16 g | 99.43% | 0.53% | Does not comply |
| 5 | 39.26 g | 99.61% | 0.38% | Does not comply |
| 6 | 54.02 g | 99.61% | 0.12% | Complies |
| 7 | 100.47 g | 99.63% | 0.11% | Complies |
| 8 | 106.94 g | 99.69% | 0.11% | Complies |
| 9 | 90.74 g | 99.86% | 0.10% | Complies |
| 10 | 81.45 g | 99.95% | 0.05% | Complies |
| 11 | 58.78 g | 99.98% | 0.02% | Complies |
| 12 | 13.37 g | 99.96% | 0.01% | Does not comply |

It was hence shown that 3-phenylpropyl-1-acetate disturbs the olfactory profile of 3-phenylpropan-1-ol and that its removal is possible by means of a method disclosed herein.

Example 2

Cinnamon Bark Oil from Sri Lanka (987 g, containing 68% cinnamaldehyde) was fractionally distilled through a column of dimensions 3×65 cm, filled with 4 mm-Wilson spirals. The distillation was carried out under a vacuum of 3-4 mbar, and the main fractions were collected at boiling temperatures of 76-79° C. The following fractions of distilled material were obtained:

| Fraction | Weight | Cinnamaldehyde | Eugenol |
| --- | --- | --- | --- |
| 1 | 60.21 g | 79.39% | 0.76% |
| 2 | 66.19 g | 91.95% | 1.33% |
| 3 | 70.74 g | 95.96% | 1.41% |
| 4 | 96.98 g | 97.85% | 1.58% |
| 5 | 97.80 g | 98.82% | 1.76% |
| 6 | 99.00 g | 98.80% | 1.92% |
| 7 | 93.28 g | 97.51% | 2.90% |
| 8 | 35.36 g | 97.01% | 2.61% |
| 9 | 36.13 g | 95.76% | 3.71% |
| residue | 280.14 g | n.d. | n.d. |

The obtained results confirm the difficulty to separate eugenol and cinnamaldehyde by means of fractional distillation.

The fractions 2-7 (524 g) were combined and contained 97.1% cinnamaldehyde and 1.9% Eugenol. These combined fractions were hydrogenated in two portions in a 300 mL stainless steel autoclave at 75-80° C. under an atmosphere of 50 bar hydrogen gas in the presence of sponge Nickel catalyst (20 g, BASF, Type Actimet 8040P). The hydrogenations were stopped after 72 hours, when the starting material and the intermediates were sufficiently consumed. The filtered crude product was diluted with heptane and washed with 10% aqueous sodium hydroxide solution and water. The organic phase was concentrated, and the obtained oily residue contained less than 0.1% of dihydroeugenol, which is the hydrogenation product of eugenol. Fractional distillation of the residue in vacuo (4-5 mbar, 83-85° C.) yielded 3-Phenylpropan-1-ol (438 g, 99.7 area-% GC-FID). The odor of the obtained distilled fractions was tested on paper stripes by an expert panel. Said expert panel constituted of 5 panelists, of which at least 4 had to agree that the aroma complies with the request, in order to have a compliant aroma. Each fraction was compared to a reference of petrochemical-derived 3-phenylpropan-1-ol. The following results were obtained:

| Fraction | Weight | 3-Phenylpropan-1-ol | Dihydroeugenol | Odor compared to reference standard |
| --- | --- | --- | --- | --- |
| 1 | 57.01 g | 94.16% | 0.21% | Does not comply |
| 2 | 61.22 g | 98.96% | 0.18% | Does not comply |
| 3 | 59.03 g | 99.48% | 0.17% | Does not comply |
| 4 | 50.96 g | 99.53% | 0.13% | Complies |
| 5 | 87.35 g | 99.61% | 0.10% | Complies |
| 6 | 131.16 g | 99.63% | 0.08% | Complies |
| 7 | 101.96 g | 99.81% | 0.05% | Complies |
| 8 | 66.57 g | 99.86% | 0.05% | Complies |

It was hence shown that dihydroeugenol disturbs the olfactory profile of 3-phenylpropan-1-ol and that its removal is possible by means of a method disclosed herein.

Example 3

O/W Cream

| Phase | Raw materials | % |
| --- | --- | --- |
| A | Water | ad 100 |
|  | Xanthan Gum | 0.50 |
|  | Pentylene Glycol | 1.50 |
| B | Cetearyl Glucoside (and) Cetearyl Alcohol | 5.00 |
|  | Butyrospermum Parkii (Shea) Butter | 3.00 |
|  | Simmondsia Chinensis (Jojoba) Seed Oil | 3.00 |
|  | Corylus Americana (Hazel) Seed Oil | 3.00 |
| C | Tocopherol | 0.10 |
| D | 3-Phenylpropan-1-ol, nature-derived | 0.5 |
| E | Aqua (and) Citric Acid | ad pH 5.5 |

The product showed a faint aromatic odour which was comparable to a product containing the same amount of petrochemical phenylpropanol instead of nature-derived phenylpropanol.

The product reached "criteria A" in a microbial challenge test according to ISO 11930, and is hence completely self-preserved.

It is believed that the present invention is not limited to the embodiments described above and that some modifications or changes may be added to the examples described without revaluing the appended claims. For example, the nature derived starting material in the Example 1 and 2, Cassia Bark Oil and Cinnamon Bark Oil, were used as starting materials respectively, but it should be understood that any nature derived starting material which can be concentrated to at least 80 wt. % of cinnamaldehyde can be used in the process of the invention, without departing from the scope of the invention.

The invention claimed is:

1. A process for manufacturing of 3-phenylpropan-1-ol from nature derived starting material, the process comprising:
obtaining the nature derived starting material from a Cassia species, a Cinnamon species, or a combination thereof;
concentrating the nature derived starting material via a chromatographical separation process or a fractional distillation process, wherein the concentrated nature derived starting material comprises not less than 80 wt. % of cinnamaldehyde;
converting the cinnamaldehyde in the nature derived starting material to 3-phenylpropan-1-ol;
purifying the 3-phenylpropan-1-ol by alkaline water extraction, wherein the purifying is carried out by extracting with alkaline water solution with addition of an organic solvent; and
distilling the 3-phenylpropan-1-ol.

2. The process according to claim 1, wherein said alkaline water solution is obtained by adding of a base selected from at least one alkali or earth alkali hydroxide to water.

3. The process according to claim 1, wherein said organic solvent is selected from heptane, toluene, tert-butyl methyl ether, 4-methyl tetrahydrofuran, or some combination thereof.

4. A process for manufacturing 3-phenylpropan-1-ol from nature derived starting material, the process comprising:
converting cinnamaldehyde in the nature derived starting material to 3-phenylpropan-1-ol by a catalytic hydrogenation, wherein the nature derived starting material comprises not less than 80 wt. % of the cinnamaldehyde;
purifying the 3-phenylpropan-1-ol by alkaline water extraction; and
distilling the 3-phenylpropan-1-ol.

5. The process according to claim 4, wherein the purifying the 3-phenylpropan-1-ol is carried out by extracting with alkaline water solution with an organic solvent.

* * * * *